US009192444B2

(12) United States Patent
Locke et al.

(10) Patent No.: US 9,192,444 B2
(45) Date of Patent: Nov. 24, 2015

(54) SEALING SYSTEMS AND METHODS EMPLOYING A SWITCHABLE DRAPE

(71) Applicant: KCI Licensing, Inc., San Antonio, TX (US)

(72) Inventors: Christopher Brian Locke, Bournemouth (GB); Timothy Mark Robinson, Basingstoke (GB); James Luckemeyer, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 378 days.

(21) Appl. No.: 13/715,982

(22) Filed: Dec. 14, 2012

(65) Prior Publication Data
US 2013/0152945 A1 Jun. 20, 2013

Related U.S. Application Data

(60) Provisional application No. 61/576,786, filed on Dec. 16, 2011.

(51) Int. Cl.
*A61F 13/00* (2006.01)
*A61B 19/08* (2006.01)
(Continued)

(52) U.S. Cl.
CPC ......... *A61B 19/088* (2013.01); *A61F 13/00068* (2013.01); *A61F 13/0253* (2013.01); *A61M 1/0088* (2013.01); *Y10T 156/1056* (2015.01)

(58) Field of Classification Search
CPC ..... A61L 15/585; A61L 24/043; A61L 15/58; A61L 15/225; A61L 15/24; A61L 15/28; A61L 24/06; A61L 15/42; A61L 26/0023; A61L 15/26; A61L 15/44; A61L 2202/181; A61L 2202/24; A61L 2430/02
USPC ............................... 128/849–856; 602/41–47
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 612111 B2 7/1991
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Michael Brown

(57) ABSTRACT

A sealing system that includes a switchable drape is presented. The drape provides enhanced sealing by using a high-strength adhesive. In one instance, the switchable drape has a plurality of perforations through which a switching solution may be delivered to the high-strength adhesive. The switching solution causes the high-strength adhesive to become less adhesive so that the switchable drape may be removed more easily. Other systems, methods, and drapes are presented.

31 Claims, 5 Drawing Sheets

(51) Int. Cl.
*A61F 13/02* (2006.01)
*A61M 1/00* (2006.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,777,016 A * | 12/1973 | Gilberts | 514/23 |
| 3,826,254 A | 7/1974 | Mellor | |
| 3,983,297 A * | 9/1976 | Ono et al. | 428/355 AC |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0062713 A1 | 3/2009 | Nash | |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 9104308 U1 | 8/1991 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | WO 2007/070269 A1 | 6/2007 |
| WO | WO 2010/129299 A2 | 11/2010 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/the British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Partial International Search Report for corresponding PCT/US2012/069920.

\* cited by examiner

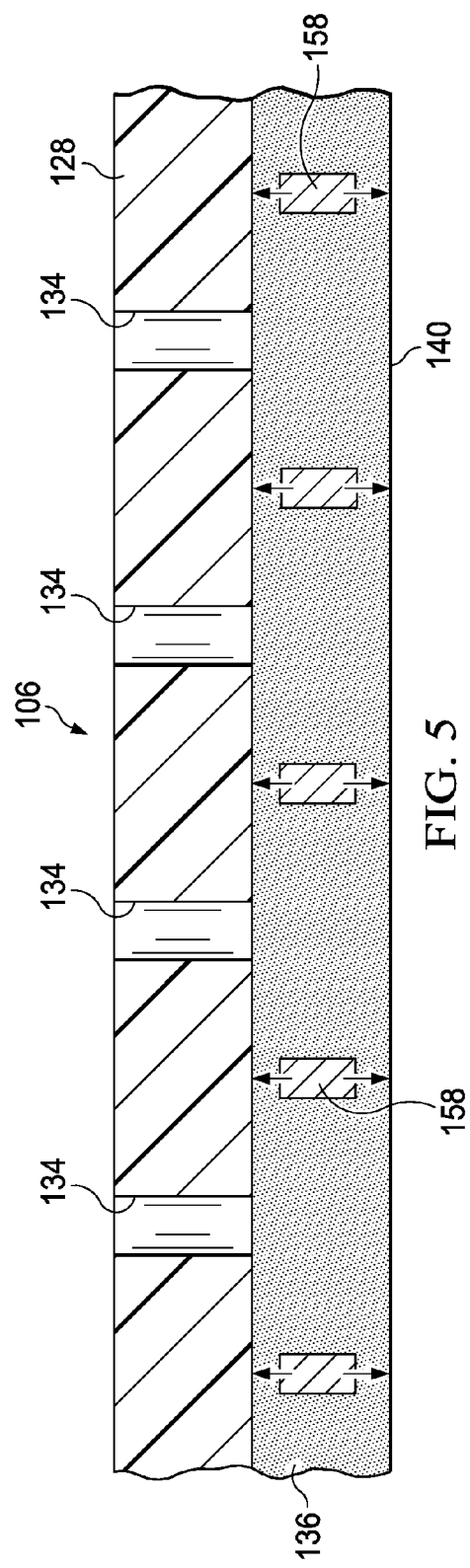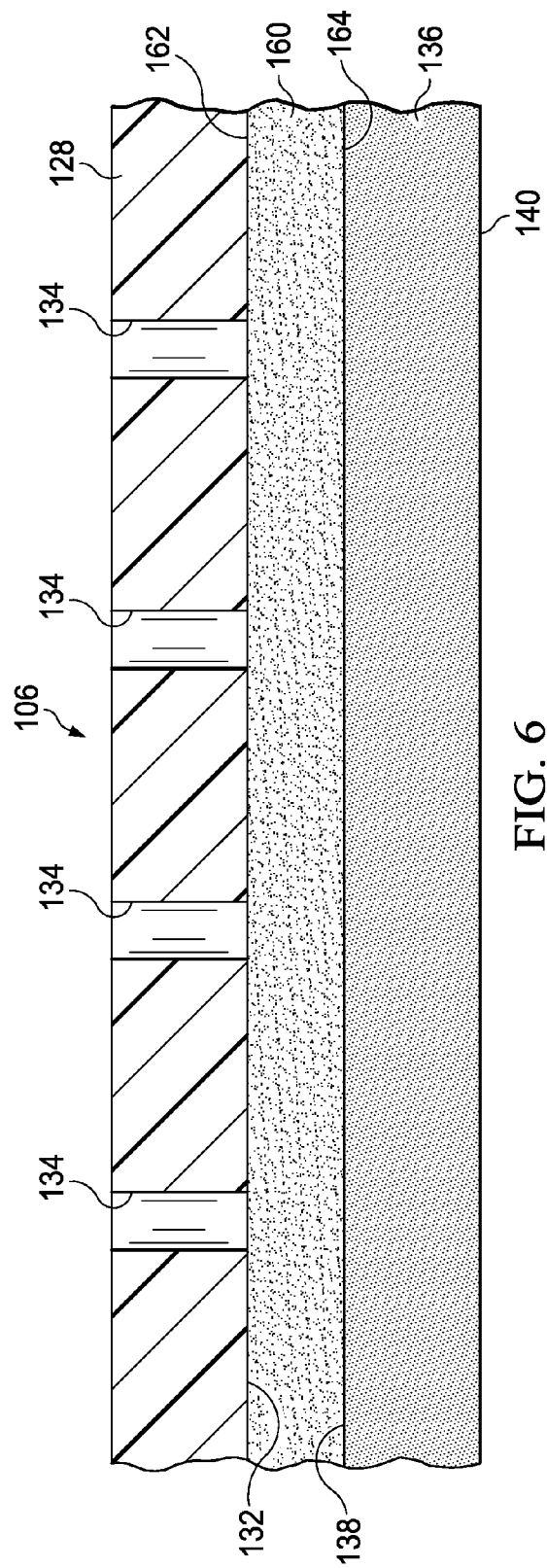

SEALING SYSTEMS AND METHODS EMPLOYING A SWITCHABLE DRAPE

CROSS-REFERENCE TO RELATED APPLICATION

This application claims priority to U.S. Provisional Patent Application No. 61/576,786 filed Dec. 16, 2011, entitled SEALING SYSTEMS AND METHODS EMPLOYING A SWITCHABLE DRAPE, the disclosure of which is hereby incorporated by reference in its entirety.

BACKGROUND OF THE INVENTION

1. Field of the Invention

The present disclosure relates generally to medical systems, devices, and methods for treating a patient with reduced pressure, and more particularly, but not by way of limitation, to sealing systems and methods employing a switchable drape.

2. Description of Related Art

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. In carrying out the treatment, a portion of the patient is sealed with a medical drape. Traditional drapes involve a balancing between strength of an adhesive on the drape and the degree of pain and disruption that will be caused when removing the drape from the patient.

SUMMARY

According to an illustrative embodiment, a sealing system for use in treating a tissue site on a patient with reduced pressure includes an outer layer formed from a drape material and has a first side and a second, patient-facing side. The outer layer is formed with a plurality of perforations extending through the outer layer. The sealing system also includes a high-strength adhesive coupled to the second, patient-facing side of the outer layer. The high-strength adhesive has a first side and a second, patient-facing side. The system further includes a switching solution. When applied to the high-strength adhesive, the switching solution changes the bond of the high-strength adhesive to lower the adhesion of the adhesive.

According to another illustrative embodiment, a method of manufacturing a switchable drape includes supplying an outer layer formed from a drape material having a first side and a second, patient-facing side. The method perforates the outer layer. The method further includes applying a high-strength adhesive to the second, patient-facing side of the outer layer. The high-strength adhesive has a first side and a second, patient-facing side. The high-strength adhesive covers the plurality of perforations. The method may also include applying a first release member to the first side of the outer layer and applying a second release member to the second, patient-facing side of the high-strength adhesive.

According to another illustrative embodiment, a kit for forming a seal over a portion of a patient's body includes a switchable drape and a switching solution. The switchable drape includes an outer layer and a high-strength adhesive. The outer layer is formed from a drape material and has a first side and a second, patient-facing side. The outer layer is formed with a plurality of perforations extending through the outer layer. The high-strength adhesive is coupled to the second, patient-facing side of the outer layer. The high-strength adhesive has a first side and a second, patient-facing side. When applied to the high-strength adhesive, the switching solution lessens the adhesive strength of the high-strength adhesive.

According to another illustrative embodiment, a method of treating a patient with reduced pressure includes deploying a manifold adjacent to the tissue site and deploying a switchable drape over the manifold and at least a portion of the epidermis adjacent to the tissue site to create a sealed space. The method also includes supplying reduced pressure to the sealed space; disposing a switching solution on the first side of the outer layer of the switchable drape; and removing the switchable drape from the patient.

According to another illustrative embodiment, a method of treating a tissue site on a patient with reduced pressure includes deploying a manifold approximate to the tissue site; deploying a medical drape over the manifold and a portion of the patient's intact skin to create a sealed space; and supplying reduced pressure to the sealed space. The method further includes terminating the reduced pressure supplied to the sealed space; creating perforations through the medical drape; and applying a switching solution onto the first side of the drape. The method also includes removing the drape.

According to another illustrative embodiment, a sealing system for use in treating a tissue site on a patient with reduced pressure includes an outer layer formed from a drape material that has a first side and a second, patient-facing side. The outer layer is formed with a plurality of perforations extending through the outer layer. The system also includes a high-strength adhesive having a first side and a second, patient-facing side. A soluble layer is coupled to the second, patient-facing side of the outer layer and the first side of the high-strength adhesive. The system further includes a switching solution. The soluble layer is operable to substantially dissolve when wetted with the switching solution.

According to another illustrative embodiment, a method of treating a tissue site on a patient with reduced pressure includes deploying a manifold proximate to the tissue site; and deploying a sealing system over the manifold and a portion of the patient's intact skin to create a sealed space containing the manifold. The sealing system includes an outer layer formed from a drape material that has a first side and a second, patient-facing side. The outer layer is formed with a plurality of perforations extending through the outer layer. The system also includes a high-strength adhesive having a first side and a second, patient-facing side and a soluble layer coupled to the second, patient-facing side of the outer layer and the first side of the high-strength adhesive. The system further includes a switching solution. The soluble layer is operable to substantially dissolve when wetted with the switching solution. The method further includes supplying reduced pressure to the sealed space, applying the switching solution onto the first side of the outer layer until the soluble layer is substantially dissolved, and removing the sealing system.

According to another illustrative embodiment, a sealing system for use in treating a tissue site on a patient with reduced pressure includes an outer layer formed from a drape material and having a first side and a second, patient-facing side, and a high-strength adhesive having a first side and a second, patient-facing side. The sealing system also includes a wicking layer disposed adjacent to at least a portion of the high-strength adhesive. The wicking layer has a plurality of wicking-layer ends extending to a periphery of the high-strength adhesive. The system also includes a switching solution. The switching solution is operable to lessen the adhesive strength of the high-strength adhesive. The wicking layer is operable to transport the switching solution from the wicking-layer ends to at least a peripheral portion of the adhesive.

According to another illustrative embodiment, a method of treating a tissue site on a patient includes deploying a manifold proximate to the tissue site. The method deploys a sealing system over the manifold and a portion of the patient's intact skin to create a sealed space containing the manifold. The sealing system includes an outer layer formed from a drape material having a first side and a second, patient-facing side and a high-strength adhesive having a first side and a second, patient-facing side. The sealing system also includes a wicking layer disposed adjacent to at least a portion of the high-strength adhesive. The wicking layer has a plurality of wicking-layer ends extending to a periphery of the high-strength adhesive. The sealing system further includes a switching solution that is operable to lessen the adhesive strength of the high-strength adhesive. The wicking layer is operable to transport the switching solution from the wicking-layer ends to at least a peripheral portion of the high-strength adhesive. The method further includes supplying reduced pressure to the sealed space; applying the switching solution onto the wicking-layer ends until the adhesive strength of the high-strength adhesive is decreased at least at a peripheral portion; and removing the sealing system.

Other aspects, features, and advantages of the illustrative embodiments will become apparent with reference to the drawings and detailed description that follow.

BRIEF DESCRIPTION OF THE DRAWINGS

FIG. 5 is a cross-sectional view of an illustrative embodiment of a switchable drape;

FIG. 6 is a cross-sectional view of an illustrative embodiment of a switchable drape;

DETAILED DESCRIPTION OF ILLUSTRATIVE EMBODIMENTS

In the following detailed description of illustrative, non-limiting embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

Figure 1:
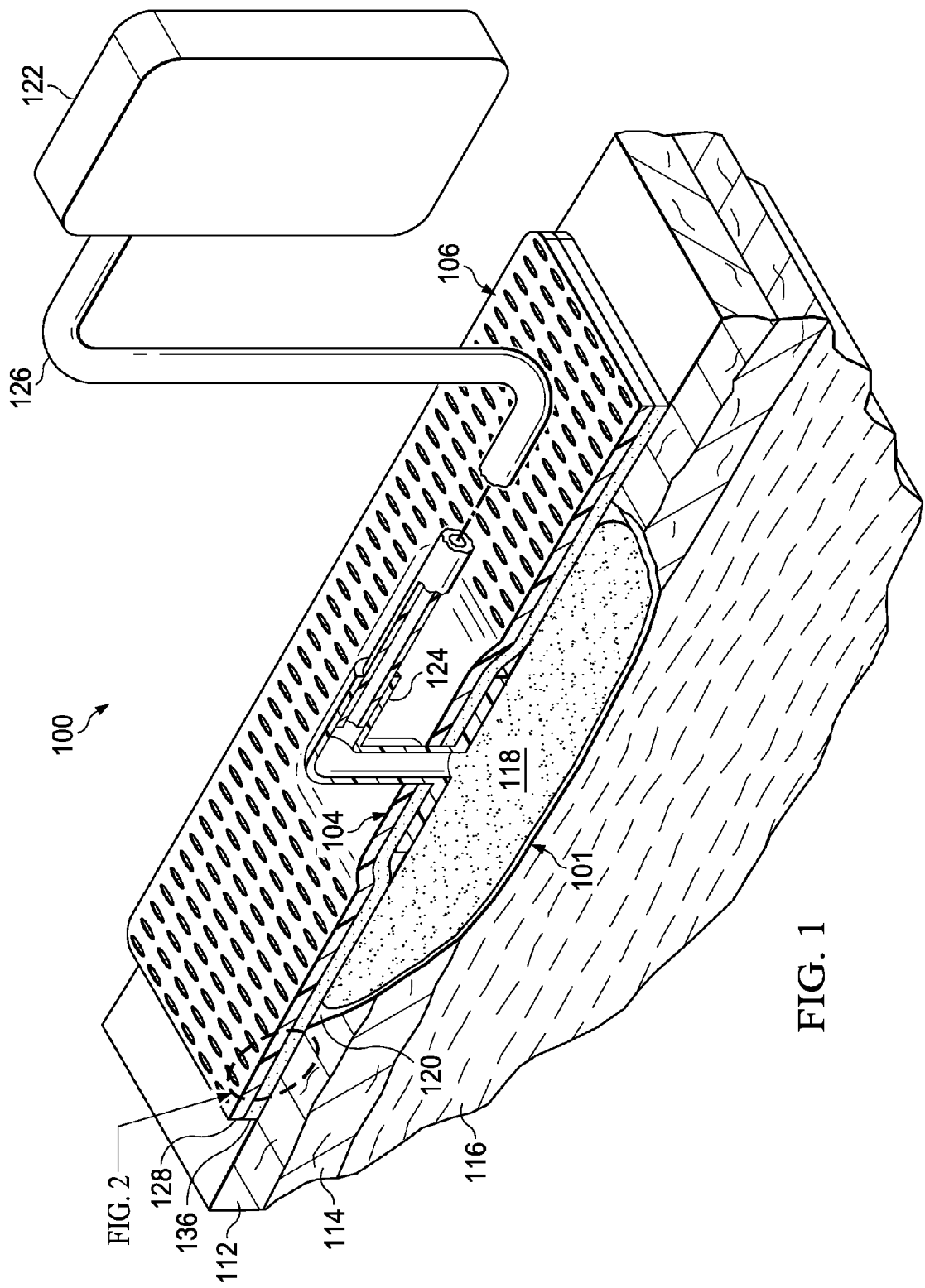
FIG. 1 is a perspective view (with a portion shown in cross section) of an illustrative embodiment of a system for treating a tissue site on a patient that employs an illustrative sealing subsystem.
Figure 2:
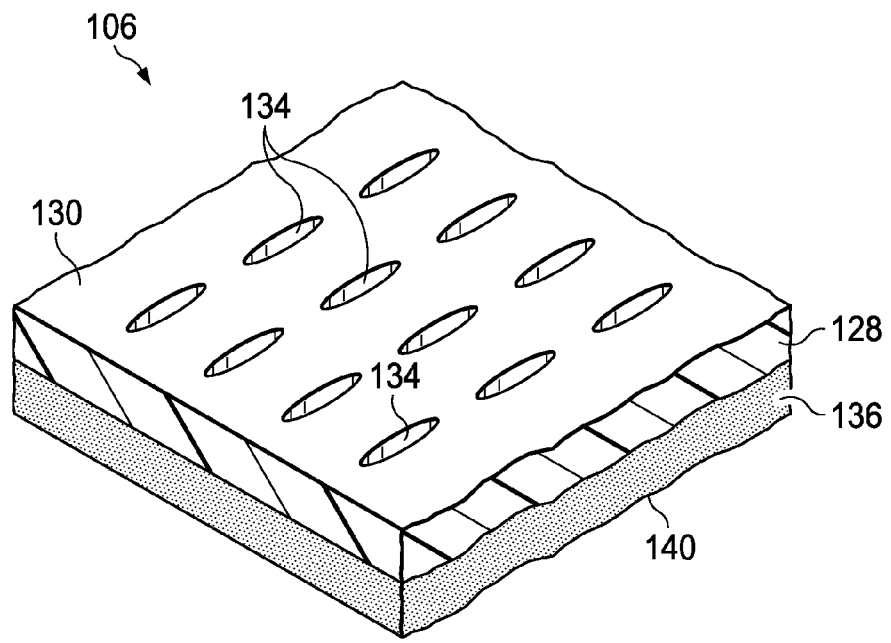
FIG. 2 is a perspective view (with a portion shown in cross section) of a portion of the illustrative sealing subsystem of FIG. 1.

Referring now to the figures and primarily to FIGS. 1-2, an illustrative embodiment of a system 100 for treating a tissue site 101 with reduced pressure is presented. The system 100 includes a sealing subsystem 104. The sealing subsystem 104 includes a switchable drape 106 that strongly adheres to an epidermis 112 adjacent the tissue site 101 during use, but is then changed or switched to a less adhering mode for removal. In this way, a strong connection may be made between the switchable drape 106 and the tissue site 101 to avoid leaks, and yet, after use, the switchable drape 106 may be removed from the tissue site 101 with minimal or at least tolerable pain.

The tissue site 101 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used throughout this document, "or" does not require mutual exclusivity. Treatment of the tissue site 101 may include removal of fluids, for example, exudate or ascites. The tissue site 101 in this example is shown as a wound that is through the epidermis 112, a dermis 114, and into a subcutaneous tissue 116, but any wound size, depth, or tissue may be involved.

In treating the tissue site 101, a manifold 118 can be deployed proximate to the tissue site 101. The manifold 118 is a substance or structure that is provided to assist in applying reduced pressure to, delivering fluids to, or removing fluids from the tissue site 101. The manifold 118 includes a plurality of flow channels or pathways that distribute fluids provided to and removed from the tissue site 101. In one illustrative embodiment, the flow channels or pathways are interconnected to improve distribution of fluids provided to or removed from the tissue site 101. The manifold 118 may comprise one or more of the following: a biocompatible material that is capable of being placed in contact with the tissue site 101 and distributing reduced pressure to the tissue site 101; devices that have structural elements arranged to form flow channels, such as, for example, cellular foam, open-cell foam, porous tissue collections, liquids, gels, and foams that include, or cure to include, flow channels; porous material, such as foam, gauze, felted mat, or any other material suited to a particular biological application; or porous foam that includes a plurality of interconnected cells or pores that act as flow channels, for example, a polyurethane, open-cell, reticulated foam such as GranuFoam® material manufactured by Kinetic Concepts, Incorporated of San Antonio, Tex.; a bioresorbable material; or a scaffold material. In some situations, the manifold 118 may also be used to distribute fluids such as medications, antibacterials, growth factors, and various solutions to the tissue site 101. Other layers may be included in or on the manifold 118, such as absorptive materials, wicking materials, hydrophobic materials, and hydrophilic materials.

In one illustrative, non-limiting embodiment, the manifold 118 may be constructed from a bioresorbable material that may remain in a patient's body following use. Suitable bioresorbable materials may include, without limitation, a polymeric blend of polylactic acid (PLA) and polyglycolic acid (PGA). The polymeric blend may also include, without limitation, polycarbonates, polyfumarates, and capralactones.

The manifold 118 may further serve as a scaffold for new cell-growth, or a scaffold material may be used in conjunction with the manifold 118 to promote cell-growth. A scaffold is a substance or structure used to enhance or promote the growth of cells or the formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The switchable drape 106 of the sealing subsystem 104 covers the manifold 118 and a portion of the epidermis 112 adjacent the tissue site 101 to form a sealed space 120. The sealed space 120 contains the manifold 118. Reduced pressure is supplied to the sealed space 120 to treat the tissue site 101 with reduced pressure.

Reduced pressure is typically a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a reduction in absolute pressure.

The reduced pressure may be delivered from a reduced-pressure source 122 to a reduced-pressure interface 124 by a reduced-pressure delivery conduit 126. The reduced-pressure interface 124 is in fluid communication with the sealed space 120.

The reduced-pressure source 122 may be any device for supplying a reduced pressure, such as a vacuum pump, wall suction, micro-pump, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa).

The reduced pressure developed by the reduced-pressure source 122 is delivered through the reduced-pressure delivery conduit 126 to the reduced-pressure interface 124. In one illustrative embodiment, the reduced-pressure interface 124 is a T.R.A.C.® Pad or Sensa T.R.A.C.® Pad available from KCI of San Antonio, Tex. The reduced-pressure interface 124 allows the reduced pressure to be delivered to the sealed space 120. In some embodiments, the reduced-pressure interface 124 may be a portion of the reduced-pressure delivery conduit 126 extending into the sealed space 120 or may simply be a vacuum port on a micro-pump that extends into the sealed space 120.

Figure 3:
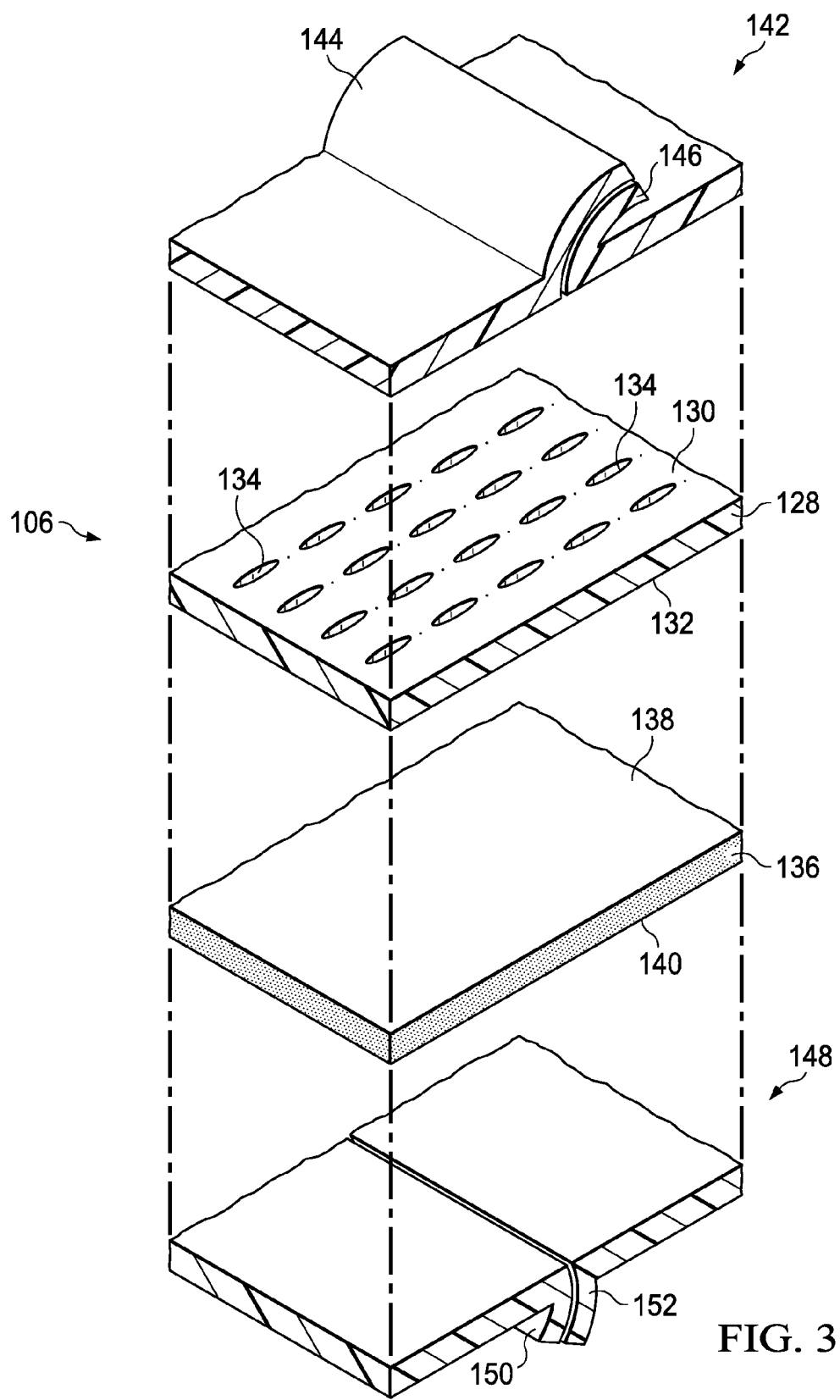
FIG. 3 is an exploded perspective view of a portion of an illustrative embodiment of a switchable drape.

The sealing subsystem 104 includes the switchable drape 106 and a switching solution. Referring now primarily to FIGS. 2 and 3, the switchable drape 106 includes an outer layer 128 formed from a drape material and having a first side 130 and a second, patient-facing side 132. The outer layer 128 is formed with a plurality of perforations 134 extending through the outer layer 128.

Figure 4:
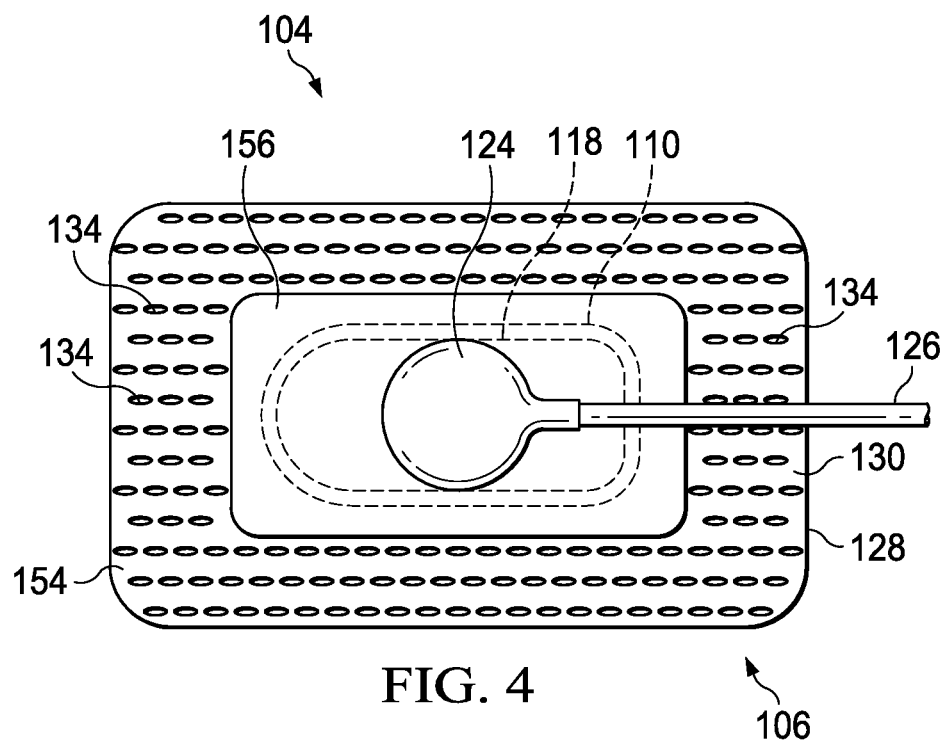
FIG. 4 is a plan view of a portion of an illustrative embodiment of a system for treating a tissue site on a patient that employs an illustrative sealing subsystem.

The plurality of perforations 134 may be apertures of any shape in which the drape material has been removed or may be slits of any shape with no drape material removed. In one illustrative embodiment, the removed drape material creates openings that have an average effective diameter in the range of about 0.05 mm to about 0.40 mm. In another illustrative embodiment, the plurality of perforations 134 may comprise a plurality of apertures, wherein the surface area of the removed material averages between about 0.2% to about 13% of the surface area of the outer layer 128. The plurality of perforations 134 may cover all of the outer layer 128 or a portion of the outer layer 128. As shown in FIG. 4, a portion of the outer layer 128 includes the plurality of perforations 134. The pitch of the perforations 134 is typically about two to about six times the thickness of a high-strength adhesive 136. For example, a switchable drape 106 having a high-strength adhesive 136 having a thickness 0.5 mm would typically have a pitch in the range of about 1.0 to about 3.0 mm in both directions. The pitch, the measurement of the distance between adjacent perforations, can vary in each direction, can be non-uniform in each direction, and may have gaps in the pattern. The size and distribution of perforations 134 are used to control the rate of solution attack on the high-strength adhesive 136. The size and distribution of perforations 134 are also used to control the tear strength of the outer layer 128.

The drape material from which the switchable drape 106 is formed may, be drape materials that provide a fluid seal. The drape material may be, for example, an impermeable or semi-permeable elastomeric material. For semi-permeable materials, the permeability must be low enough that for a given reduced-pressure source, the desired reduced pressure may be maintained. Elastomeric material generally refers to a polymeric material that has rubber-like properties. More specifically, most elastomers have ultimate elongations greater than 100% and a significant amount of resilience. The resilience of a material refers to the ability of the material to recover from an elastic deformation. Examples of elastomers include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, examples of drape materials include a silicone drape, a 3M Tegaderm® drape, or a polyurethane (PU) drape such as one available from Avery Dennison Corporation of Pasadena, Calif.

The drape material may be a high-moisture-vapor-transfer-rate drape material. "Moisture vapor transmission rate" or "MVTR" represents the amount of moisture that can pass through a material in a given period of time. For example, the high-moisture-vapor-transfer-rate drape may have an MVTR greater than about 300 g/m$^2$/24 hours or, more typically, greater than about 1000 g/m$^2$/24 hours or more. Additional examples of suitable drape materials include one or more of the following: hydrophilic polyurethanes, cellulosics, hydrophilic polyamides, polyvinyl alcohol, polyvinyl pyrrolidone, hydrophilic silicone polymers, hydrophilic acrylics, hydrophilic silicone elastomers and copolymers of these. As one specific, illustrative, non-limiting embodiment, the drape material may be a breathable cast mat polyurethane film sold under the name INSPIRE 2301 from Exopack Advanced Coatings of Wrexham, United Kingdom, having an MVTR (inverted cup technique) of 14500-14600 g/m$^2$/24 hours. The outer layer 128 may have various thicknesses, such as about 10 to about 100 microns (μm), e.g., 15, 20, 30, 40, 50, 60, 70, 80, 90, 100 microns or any number in the stated range.

The switchable drape 106 also includes the high-strength adhesive 136, which has a first side 138 and a second, patient-facing side 140. It should be noted that the switchable drape 106 does not leak through the plurality of perforations 134 because the high-strength adhesive 136 covers the plurality of perforations 134. For this reason, the high-strength adhesive 136 is typically applied to the second, patient-facing side 132 of the outer layer 128 after the plurality of perforations 134 have been formed.

The high-strength adhesive 136 typically has an adhesive strength one to two times stronger than adhesives used on most medical drapes. For example, without limitation, one medical drape, for example, MED1827A by Avery, has a bond strength to polythene, 90 degree, of 144 N/m. Whereas, according to one illustrative embodiment, a switchable drape produced according to the embodiments described herein may have a bond strength in the range of greater than about 144 N/m to about 288 N/m under similar testing conditions. The high-strength adhesive 136 typically has a thickness in the range of about 0.3 mm to about 1.5 mm. The high-strength adhesive 136 may be formed from an acrylic adhesive or other adhesive. The high-strength adhesive 136 is typically soft enough and thick enough that the high-strength adhesive 136 fills any cracks or crevices in the epidermis 112 adjacent the tissue site 101 to form a strong fluid seal and maintains that seal when negative pressure is applied to the sealed space 120.

As shown best in FIG. 3, the first side 130 of the outer layer 128 may be covered by a first release member 142. The first release member 142 may be a material that seals the surface of or provides additional handling rigidity to the outer layer 128. The first release member 142 may also be a material that is removable. The first release member 142 may comprise one or more of the following: a polyurethane film, high density polyethylene, a high-MVTR film, polymers such as acrylic copolymers, polyvinyl acetate, polyether block amide copolymers (PEBAX), polyvinyl alcohol and copolymers, polyamide, polyvinylchloride, or polyvinylidene chloride. As shown in FIG. 3, the first release member 142 may be a two-part member having two gripping portions 144, 146 to facilitate removal. The first release member 142 may be retained only during deployment of the outer layer 128 and then removed. Alternatively, the first release member 142 may remain in place covering the plurality of perforations 134 until removal of the outer layer 128 from the tissue site 101 is desired. In this latter situation, the first release member 142 prevents accidental exposure of the high-strength adhesive 136 to a switching solution through the plurality of perforations 134.

As shown in FIG. 3, a second release member 148, which is analogous to the first release member 142, may be used to cover the second, patient-facing side 140 of the high-strength adhesive 136 prior to use. The second release member 148 is removed before the high-strength adhesive 136 is deployed against the epidermis 112 adjacent the tissue site 101. The second release member 148 may include a first gripping member 150 and a second gripping member 152 to facilitate removal of the second release member 148 from the high-strength adhesive 136.

As previously noted, the plurality of perforations 134 may be formed with or without removing portions of the drape material. If no material is removed, the perforations may be formed, for example, without limitation, as slits such as half-moon slits, which are then covered on the second, patient facing side 132 by the high-strength adhesive 136. In this way, the plurality of perforations 134 act as small valves and minimize exposure of the high-strength adhesive 136 to the first side 130 of the outer layer 128. If the drape material is removed in forming the plurality of perforations 134, the high-strength adhesive 136 may extend through the perforations 134 and causes a tackiness to be experienced on the first side 130 of the outer layer 128. In this case, the first release member 142 may be left in place to cover the perforations 134 on the first side 130 of the outer layer 128 until removal of the switchable drape 106 is desired. Alternatively, a powder or sealing agent may be applied on the first side 130 of the outer layer 128.

The switching solution is a solution that when applied to the high-strength adhesive 136 lessens the adhesive strength of the high-strength adhesive 136. In other words, if the high-strength adhesive 136 has an initial adhesive strength of $A_1$, after application of the switching solution, the high-strength adhesive 136 has a lesser adhesive strength, $A_2$, for example, $A_2<A_1$. The adhesive strength $A_2$ after application of the switching solution may be less than about 70% of the original adhesive strength, 70% $A_1$, or even less, for example, 60% $A_1$, 50% $A_1$, 40 $A_1$, 30% $A_1$, 20% $A_1$, 10% $A_1$, or 0% $A_1$. Many permutations are possible, but in one embodiment, the switchable drape 106 has twice the adhesive strength of a traditional drape, but at removal has only half or less than half of the adhesive strength of a traditional drape.

The switching solution may be one or more of the following: alcohols, such as methanol, propyl alcohols, and other alcohols such as butanols, esters such as butyl ethanoate (acetate), ketones, such as propanone (acetone), natural oils such as linseed, soyer, and blends of all these materials with each other, and may also be blended with water. The switching solution may contain additional components such as a local pain killer or analgesic, for example, Lidocaine, prilocalne, bupivacaine, or mixtures of these, or another suitable substance. The switching solution may be kept in a bottle, vial, pouch, sealed wipe, or other convenient storage or delivery means.

The switchable drape 106 may be formed in numerous ways. According to one illustrative embodiment, the outer layer 128 is formed from a drape material. The plurality of perforations 134 are then formed through the outer layer 128 by punching, cutting, or drilling, for example. The high-strength adhesive 136 is applied to the second, patient-facing side 132 of the outer layer 128. The first release member 142 is applied to the first side 130 of the outer layer 128. The second release member 148 is applied to the second, patient-facing side of the high-strength adhesive 136.

In operation, according to one illustrative embodiment, the manifold 118 is deployed adjacent to the tissue site 101. The switchable drape 106 is deployed over the manifold 118 and a portion of the epidermis 112 adjacent to the tissue site 101 to create the sealed space 120. If not already applied, the reduced-pressure interface 124 is applied to provide fluid communication from a point exterior of the switchable drape 106 to the sealed space 120. A reduced-pressure delivery conduit 126 is fluidly coupled between the reduced-pressure interface 124 and the reduced-pressure source 122. The reduced-pressure source 122 is activated and reduced pressure is supplied to the sealed space 120 and distributed by the manifold 118. After a desired treatment time has passed, the switchable drape 106 is removed.

The switchable drape 106 is removed by removing the first release member 142, if applicable, and applying the switching solution on the first side 138 of the switchable drape 106. The switching solution travels through the plurality of perforations 134 and wets the high-strength adhesive 136. Wetting the high-strength adhesive 136 causes the adhesive strength of the high-strength adhesive 136 to decrease. The outer layer 128 of the switchable drape 106 is then removed from the patient 102.

In another illustrative embodiment, a micro-pump is used as the reduced-pressure source 122. In this embodiment, the micro-pump is coupled to the switchable drape 106. In another illustrative embodiment, the switchable drape 106 may be used as a dressing without reduced pressure.

Referring now primarily to FIG. 4, a portion of another illustrative embodiment of a sealing subsystem 104 is presented. The sealing subsystem 104 is analogous in most respects to the sealing subsystem 104 of FIGS. 1-3, and accordingly, some parts are labeled but not further described here. This embodiment differs primarily in that the plurality of perforations 134 are formed only on a peripheral portion 154 of the outer layer 128. The peripheral portion 154 is an outer band on the outer layer 128 that is sized to be exclusively or nearly exclusively over the epidermis 112 adjacent the tissue site 101. In contrast, a central portion 156 of the outer layer 128 is over the tissue site 101 and does not have perforations 134. The high-strength adhesive (analogous to 136 in FIG. 3) is applied to the second, patient-facing side 132 of the outer layer 128 only on the peripheral portion 154. A lower adhesive strength adhesive is used on the central portion 156 of the second, patient-facing side 132 of the outer layer 128. This approach may allow for an even stronger adhesive to be used as the high-strength adhesive 136 without causing undue pain to the patient.

Referring now primarily to FIG. 5, a portion of another illustrative embodiment of a switchable drape 106 is presented. The switchable drape 106 is analogous in most respects to the switchable drape 106 of FIGS. 1-3, and accordingly, some parts are labeled but not further described here. This embodiment differs primarily in that the high-strength adhesive 136 further comprises a plurality of expansion members 158. The expansion members 158 are configured to expand primarily perpendicularly to the second, patient-facing side 132 of the outer layer 128 when activated by the switching solution. The expansion members 158 may be, for example, compressed foam, where the foam is compressed and cooled below a transition temperature to temporarily fix the "set." The "set" is released when the foam is contacted by a plasticizer contained within the switching solution. For example, a polyvinyl acetate foam could be set in this way and contacted with ethanol to plasticize the foam, thereby releasing the "set" and allowing the foam to expand. The expansion members 158 may also contain a foaming agent, such as a bicarbonate salt. When using the bicarbonate salt, the switching solution may include water and a weak acid (such as citric acid). When the water and the weak acid come into contact with the bicarbonate salt, carbon dioxide gas is released, providing an expanding force. The expansion members 158 expand perpendicularly to the epidermis 112 adjacent the tissue site 101 when activated by the switching solution, thereby lifting the outer layer 128 and weakening the high-strength adhesive 136. This action facilitates removal of the switchable drape 106 from the patient.

Referring now primarily to FIG. 6, a portion of another illustrative embodiment of a switchable drape 106 is presented. The switchable drape 106 is analogous in most respects to the switchable drape 106 of FIGS. 1-3, and accordingly, some parts are labeled but not further described here. This embodiment differs primarily in that the switchable drape 106 includes a soluble layer 160 between the outer layer 128 and the high-strength adhesive 136. The soluble layer 160 has a first side 162 and a second, patient-facing side 164. The first side 162 is adjacent to the second, patient facing side 132 of the outer layer 128. The second, patient-facing side 164 is adjacent to the first side 138 of the high-strength adhesive 136.

The soluble layer 160 is such that when the switching solution or another solution (for example, water or aqueous solutions) is applied, the soluble layer 160 dissolves, or substantially dissolves, thereby loosening the soluble layer's grip on the first side 138 of the high-strength adhesive 136. In this way, the outer layer 128 may be quickly removed. The soluble layer 160 may also keep the high-strength adhesive 136 from entering the perforations 134 during manufacture.

Figure 7:
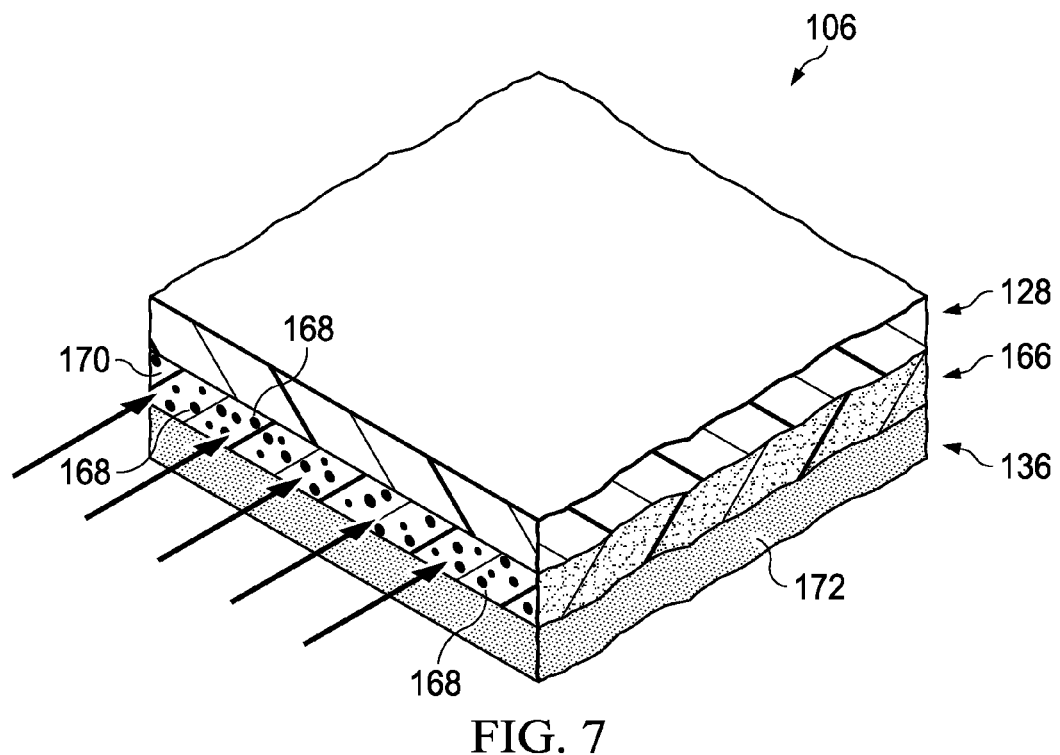
FIG. 7 is a perspective view (with a portion shown in cross section) of an illustrative embodiment of a switchable drape.

Referring now primarily to FIG. 7, a portion of another illustrative embodiment of a switchable drape 106 is presented. The switchable drape 106 is analogous in most respects to the switchable drape 106 of FIGS. 1-3, and accordingly, some parts are labeled but not further described here. This embodiment differs primarily in that a wicking layer 166 is disposed between the outer layer 128 and the high-strength adhesive 136. The wicking layer 166 may be separate as shown or embedded in the high-strength adhesive 136. The wicking layer 166 may be a lightweight, open material of woven or non-woven material. In some embodiments, the wicking layer 166 uses single threads. The threads of the woven or non-woven material of the wicking layer 166 may be continuous, may be scatter coated, or randomly distributed in the wicking layer 166. The random fiber distribution may disrupt leak paths that may occur from the perimeter to the center.

The wicking layer 166 has a plurality of wicking-layer ends 168 at an edge 170 of the switchable drape 106. The wicking layer 166 is operable to transport the switching solution from the wicking-layer ends 168 to at least a peripheral portion 172 of the high-strength adhesive 136. The peripheral portion 172 may be similar to the peripheral portion 154 and may be an outer band of the adhesive layer 136 that is sized to be exclusively or nearly exclusively over the epidermis 112 adjacent the tissue site 101. Because the wicking layer 166 moves the switching solution from the edge 170 inboard and exposes the switching solution to the high-strength adhesive 136 in the process, the outer layer 128 does not require perforations. If the wicking layer 166 causes a leak, the leak will not be to the tissue site 101 but to the reduced-pressure interface 124 as the adhesive layer 136 is interposed between the wicking layer 166 and the tissue site 101. The wicking layer 166 may be laminated with a solvent soluble coating to decrease instances of leaks.

According to an illustrative embodiment associated FIG. 7, a tissue site on a patient is treated by applying a manifold (not shown, but analogous to 118) over the tissue and then applying the switchable drape 106 over the manifold and a portion of the epidermis adjacent to the tissue site to form a sealed space. Reduced pressure is applied to the sealed space to provide a reduced-pressure treatment. When a desired treatment time has elapsed, the user applies a switching solution to the wicking-layer ends 168. The switching solution is wicked into the fibers of the wicking layer 166. The high-strength adhesive 136 is thereby wetted by the switching solution on at least the peripheral portion 172 of the high-strength adhesive 136. As a result, the high-strength adhesive 136 loses tackiness. After losing sufficient tackiness in the high-strength adhesive 136, the outer layer 128 is removed.

Figure 8:
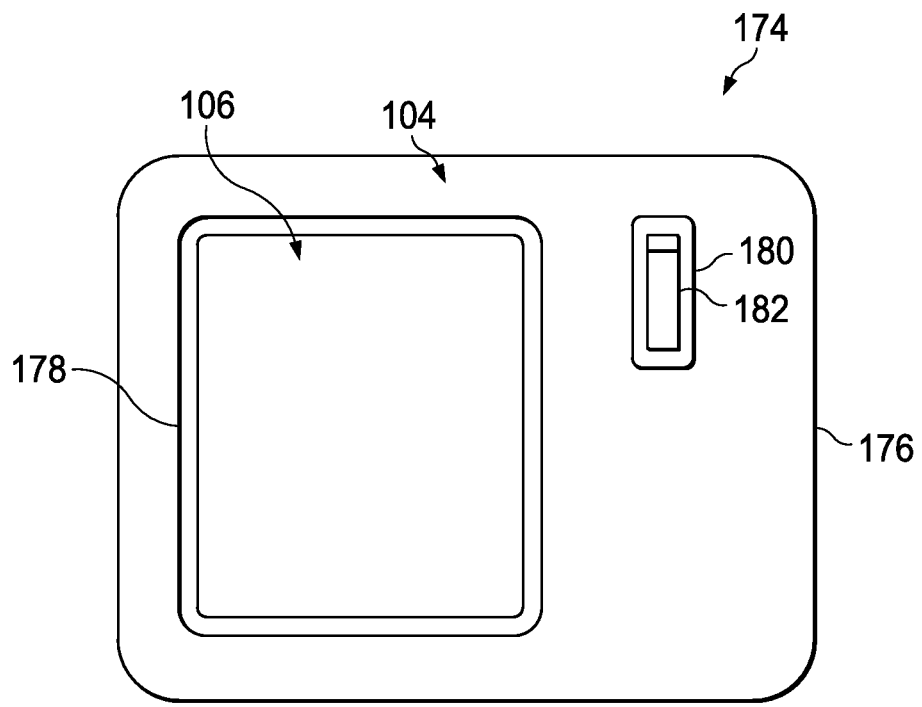
FIG. 8 is a plan view of an illustrative embodiment of a kit for forming a seal over the portion of a patient's body.

Referring now primarily to FIG. 8, the sealing subsystem 104 may be stored and presented for use in a kit 174. The kit 174 may have a package or container 176. The container 176 may have a first compartment 178 for receiving the switchable drape 106. The container 176 may have a second compartment 180 for receiving a container, vial 182, wipe, or other item containing the switching solution. Another compartment (not shown) may be added to include skin preparation materials. In one embodiment, sealed skin preparation wipes may be disposed in the second compartment 180. One skin preparation wipe may be used to prepare the skin and another to rub on the first side 130 of the outer layer 128 to remove the outer layer 128 after use of the sealing subsystem 104.

According to an alternative method for treating a tissue site, a manifold is deployed proximate to the tissue site. The manifold and a portion of the patient's intact skin are covered with a medical drape (for example, switchable drape 106 but without perforations) to form a sealed space. Reduced pressure is delivered to the sealed space. After a desired treatment time, the reduced pressure is terminated. A hand tool is then used to form a plurality of perforations in the medical drape around the tissue site, and a switching solution is applied over the perforations. The switching solution causes the adhesive strength of the adhesive on the medical drape to decrease. The medical drape is removed.

In some illustrative embodiments, the perforations 134 may be located only in certain places or may be located in key places or concentrated in certain places for different effects. For example, as explained in connection with FIG. 4, the perforations 134 may only be in a peripheral portion 154. In addition, the perforations 134 may be concentrated to form tear lines or tear patterns. The tear patterns or tear lines allow the switchable drape 106 to be torn by hand along the tear line or tear pattern. In this way, the switchable drape 106 may be sized by hand with out tools. In some embodiments, the perforations 134 may be located at locations, for example, over a joint, to facilitate stretching of the switchable drape 106.

The systems, sealing subsystems, and switchable drapes herein may offer numerous advantages. Some of the advantages may include that the switchable drape may be "switched"—activated to have less adhesive strength—without requiring external energy; use of the switchable drape does not require special skills from current practices; the system is cost effective; the switchable drape provides an improved seal with the epidermis adjacent the tissue site; and the switchable drape can be used with existing systems. Other benefits and advantages exist.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate as understood by one skilled in the art.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A sealing system for use in treating a tissue site on a patient with reduced pressure, the sealing system comprising:
   an outer layer formed from a drape material and having a first side and a second side, wherein the outer layer is formed with a plurality of slits extending through the outer layer and having no drape material removed from the outer layer;
   a high-strength adhesive coupled to the second side of the outer layer, wherein the high-strength adhesive has a first side, a second side, and a tackiness; and
   a switching solution, wherein when the switching solution is applied to the high-strength adhesive, the tackiness of the high-strength adhesive decreases.

2. The system of claim 1, wherein the outer layer comprises a high-moisture-vapor-transfer rate material.

3. The system of claim 1, wherein the outer layer has a thickness in the range of about 5 microns to about 60 microns.

4. The system of claim 1, wherein the plurality of slits comprise a plurality of apertures having an average effective diameter between about 0.05 mm and about 0.4 mm.

5. The system of claim 1, wherein the plurality of slits comprise a plurality of apertures, and a surface area of the drape material removed to form the plurality of apertures is between about 0.2% to about 13% of surface area of the outer layer.

6. The system of claim 1, wherein the high-strength adhesive comprises an acrylic adhesive.

7. The system of claim 1, wherein the high-strength adhesive further comprises expansion members that are configured to expand primarily perpendicularly to the second side of the outer layer when activated by the switching solution.

8. The system of claim 1, wherein the switching solution comprises alcohol.

9. The system of claim 1, wherein the switching solution further comprises a local pain killer.

10. The system of claim 1, further comprising a first release member coupled to the first side of the outer layer and a second release member coupled to the second side of the high-strength adhesive.

11. A method of manufacturing a switchable drape, the method comprising:
   supplying an outer layer formed from a flexible drape material having a first side and a second side;
   perforating the outer layer to form a plurality of perforations;
   applying a high-strength adhesive to the second side of the outer layer, wherein the high-strength adhesive has a first side and a second side and wherein the high-strength adhesive covers the plurality of perforations;
   applying a first release member to the first side of the outer layer; and
   applying a second release member to the second side of the high-strength adhesive.

12. The method of claim 11, wherein perforating the outer layer comprises perforating a peripheral portion of the outer layer.

13. The method of claim 11, wherein perforating the outer layer comprises perforating the outer layer in a tear pattern to facilitate tearing of the drape material of the outer layer.

14. The method of claim 11, further comprising disposing expansion members in the high-strength adhesive, wherein the expansion members are configured to primarily expand perpendicularly to the second side of the outer layer.

15. A kit for forming a seal over a portion of a patient's body, the kit comprising:
- a switchable drape;
- a switching solution;
- wherein the switchable drape comprises:
  - an outer layer formed from a drape material and having a first side and a second side, wherein the outer layer is formed with a plurality of perforations extending through the outer layer,
  - a high-strength adhesive coupled to the second side of the outer layer, wherein the high-strength adhesive has a first side and a second side,
  - a first release member releasably coupled to the first side of the outer layer, and
  - a second release member releasably coupled to the second side of the high-strength adhesive; and
- wherein, once applied, the switching solution lessens the adhesive strength of the high-strength adhesive.

16. A method of treating a patient with reduced pressure, the method comprising:
- deploying a manifold adjacent to the tissue site;
- deploying a switchable drape over the manifold to create a sealed space, wherein the switchable drape comprises:
  - an outer layer formed from a drape material and having a first side and a second side, wherein the outer layer is formed with a plurality of perforations extending through the outer layer, and
  - a high-strength adhesive coupled to the second side of the outer layer, wherein the high-strength adhesive has a first side and a second side;
- supplying reduced pressure to the sealed space;
- disposing a switching solution on the first side of the outer layer of the switchable drape; and
- removing the switchable drape from the tissue site.

17. A method of treating a tissue site on a patient with reduced pressure, the method comprising:
- deploying a manifold proximate to the tissue site;
- deploying a medical drape over the manifold to create a sealed space;
- supplying reduced pressure to the sealed space;
- terminating the reduced pressure supplied to the sealed space;
- creating perforations through the medical drape;
- applying a switching solution onto the first side of the drape; and
- removing the drape.

18. A sealing system for use in treating a tissue site on a patient with reduced pressure, the system comprising:
- an outer layer formed from a drape material and having a first side and a second side, wherein the outer layer is formed with a plurality of perforations extending through the outer layer;
- a high-strength adhesive having a first side and a second side;
- a soluble layer coupled to the second side of the outer layer and the first side of the high-strength adhesive; and
- a switching solution, wherein the soluble layer is operable to substantially dissolve when wetted with the switching solution.

19. The sealing system of claim 18, wherein the switching solution is operable to lessen the adhesive strength of the high-strength adhesive.

20. A method of treating a tissue site on a patient with reduced pressure, the method comprising:
- deploying a manifold proximate to the tissue site;
- deploying a sealing system over the manifold to create a sealed space containing the manifold, wherein the sealing system comprises:
  - an outer layer formed from a drape material and having a first side and a second side, wherein the outer layer is formed with a plurality of perforations extending through the outer layer,
  - a high-strength adhesive having a first side and a second side,
  - a soluble layer coupled to the second side of the outer layer and the first side of the high-strength adhesive, and
  - a switching solution, wherein the switching solution is operable to substantially dissolve and decrease the adhesive strength of the of the high-strength adhesive;
- supplying reduced pressure to the sealed space;
- applying the switching solution onto the first side of the outer layer until the soluble layer is substantially dissolved; and
- removing the sealing system.

21. A sealing system for use in treating a tissue site on a patient with reduced pressure, the system comprising:
- an outer layer formed from a drape material and having a first side and a second side;
- a high-strength adhesive having a first side and a second side;
- a wicking layer disposed adjacent to at least a portion of the high-strength adhesive and having a plurality of wicking-layer ends extending to at least a peripheral portion of the high-strength adhesive;
- a switching solution, wherein the switching solution is operable to lessen the adhesive strength of the of the high-strength adhesive; and
- wherein the wicking layer is operable to transport the switching solution from the wicking-layer ends to at least the peripheral portion of the adhesive.

22. A method of treating a tissue site on a patient, the method comprising:
- deploying a manifold proximate to the tissue site;
- deploying a sealing system over the manifold to create a sealed space containing the manifold, wherein the sealing system comprises:
  - an outer layer formed from a drape material and having a first side and a second side,
  - a high-strength adhesive having a first side and a second side,
  - a wicking layer adjacent to at least a portion of the high-strength adhesive and having a plurality of wicking-layer ends extending to at least a peripheral portion of the high-strength adhesive,
  - a switching solution, wherein the switching solution is operable to lessen the adhesive strength of the of the high-strength adhesive, and
  - wherein the wicking layer is operable to transport the switching solution from the plurality of wicking-layer ends to at least the peripheral portion of the adhesive;
- supplying reduced pressure to the sealed space;
- applying the switching solution onto the wicking-layer ends until the adhesive strength of the high-strength adhesive is decreased at least at the peripheral portion; and
- removing the sealing system.

23. The system of claim 1, further comprising:
- a first release member having gripping portions and coupled to the first side of the outer layer; and
- a second release member having gripping portions and coupled to the second side of the high-strength adhesive.

24. The system of claim 1, wherein the slits comprise half-moon slits.

25. The system of claim 1, wherein the switching solution is adapted to decrease the tackiness of the high-strength adhesive between about 0% and about 70%.

26. The system of claim 1, wherein the switching solution is adapted to decrease the tackiness of the high-strength adhesive by about 50%.

27. The system of claim 1, wherein the high-strength adhesive further comprises expansion members formed of a compressed and cooled foam and disposed within the high-strength adhesive, the expansion members configured to expand primarily perpendicularly to the second-side of the outer layer when activated by the switching solution.

28. The system of claim 21, wherein the outer layer has a plurality of perforations extending through the outer layer.

29. The system of claim 1, wherein the perforations have a pitch in the range of about 1.0 mm to about 3.0 mm.

30. The system of claim 1, wherein the high-strength adhesive has a bond strength in the range of greater than about 144 N/M to about 288 N/m.

31. The system of claim 1, wherein the high-strength adhesive has a bond strength in the range of greater than about 144 N/M to about 288 N/m, and the switching solution is adapted to decrease the tackiness of the high-strength adhesive by about 50%.

* * * * *